US00PP33714P2

(12) United States Plant Patent
Korlipara

(10) Patent No.: US PP33,714 P2
(45) Date of Patent: Nov. 30, 2021

(54) ***ECHINACEA* PLANT NAMED 'TNECHDSW'**

(50) Latin Name: ***Echinacea* spp.**
Varietal Denomination: TNECHDSW

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/207,106

(22) Filed: Mar. 19, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

PUBLICATIONS https://www.gardencentermag.com/article/terra-nova-nurseries-new-echinacea/; Mar. 25, 2020; 1 page.*

* cited by examiner

*Primary Examiner* — Kent L Bell
(74) *Attorney, Agent, or Firm* — Klarquist Sparkman, LLP

(57) ABSTRACT

A new and distinct *Echinacea* plant named 'TNECHDSW' characterized by a very large number of medium inflorescences starting in the first season, very long bloom time with excellent rebloom, a very upright, very compact habit, bright rose-pink ray florets surrounding dark cones, ray florets held horizontally, strong upright stems, and excellent vigor.

2 Drawing Sheets

Botanical denomination: *Echinacea* spp.
Variety designation: 'TNECHDSW'.
Trademark Designation: DARK SHADOWS WICKED™.

BACKGROUND OF THE INVENTION

The present invention relates to a new and distinct cultivar of *Echinacea* and given the cultivar name 'TNECHDSW'. *Echinacea* is in the family Asteraceae. The new cultivar is part of a planned breeding program for a container and garden series with compact habits and profuse inflorescences. The exact parents of this selection are unknown, unnamed, proprietary interspecific hybrids bred from *Echinacea paradoxa, Echinacea purpurea*, and *Echinacea tennesseensis*.

Compared to *Echinacea* 'TNECHKR' (U.S. Plant Pat. No. 28,768), the new cultivar is shorter and has brighter and softer colored ray florets.

This new *Echinacea* cultivar is uniquely distinguished by:

1. A very large number of medium inflorescences starting in the first season,
2. very long bloom time with excellent rebloom,
3. very upright, very compact habit,
4. bright rose-pink ray florets surrounding dark cones,
5. ray florets held horizontally,
6. strong upright stems, and
7. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding asexual propagations. The present invention has not been evaluated under all possible environmental conditions. The phenotype may vary with variations in environment without a change in the genotype of the plant.

DETAILED PLANT DESCRIPTION

Figure 1:
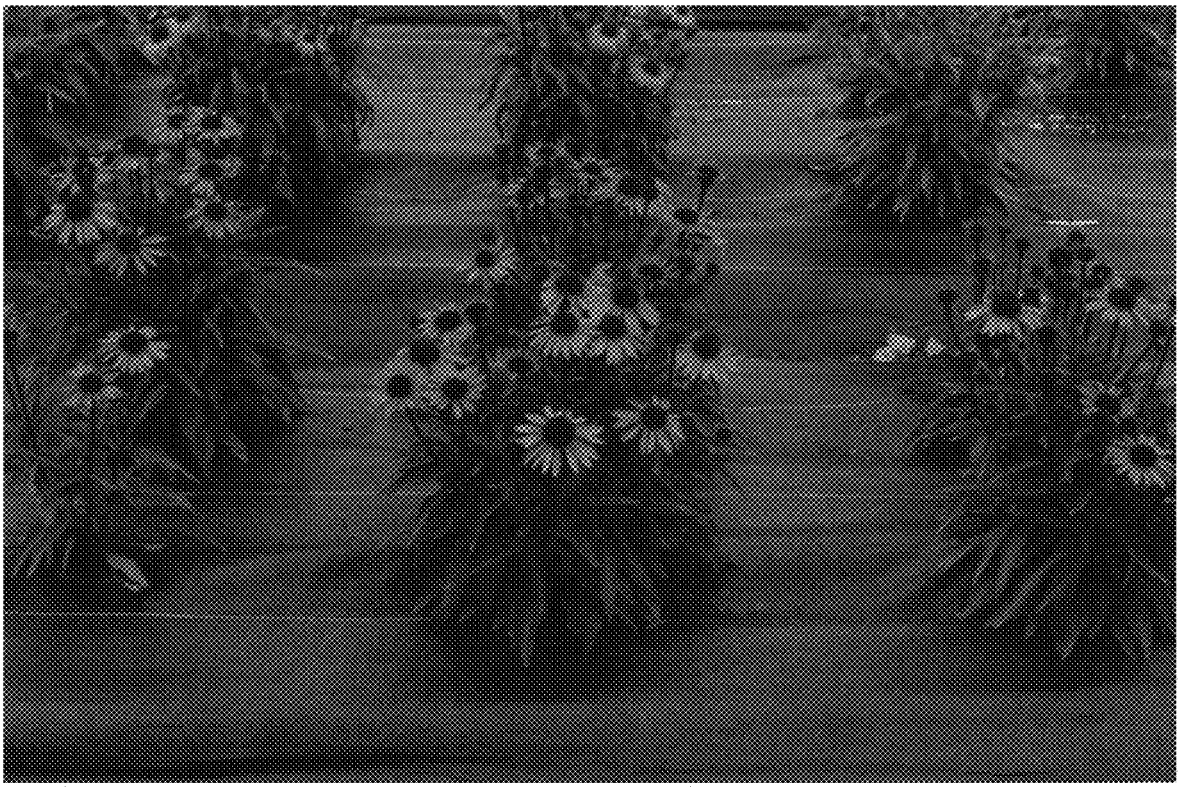
FIG. 1 shows nine-month-old *Echinacea* 'TNECHDSW' plants growing in the trial field in full sun in late July in Canby, Oreg.
Figure 2:
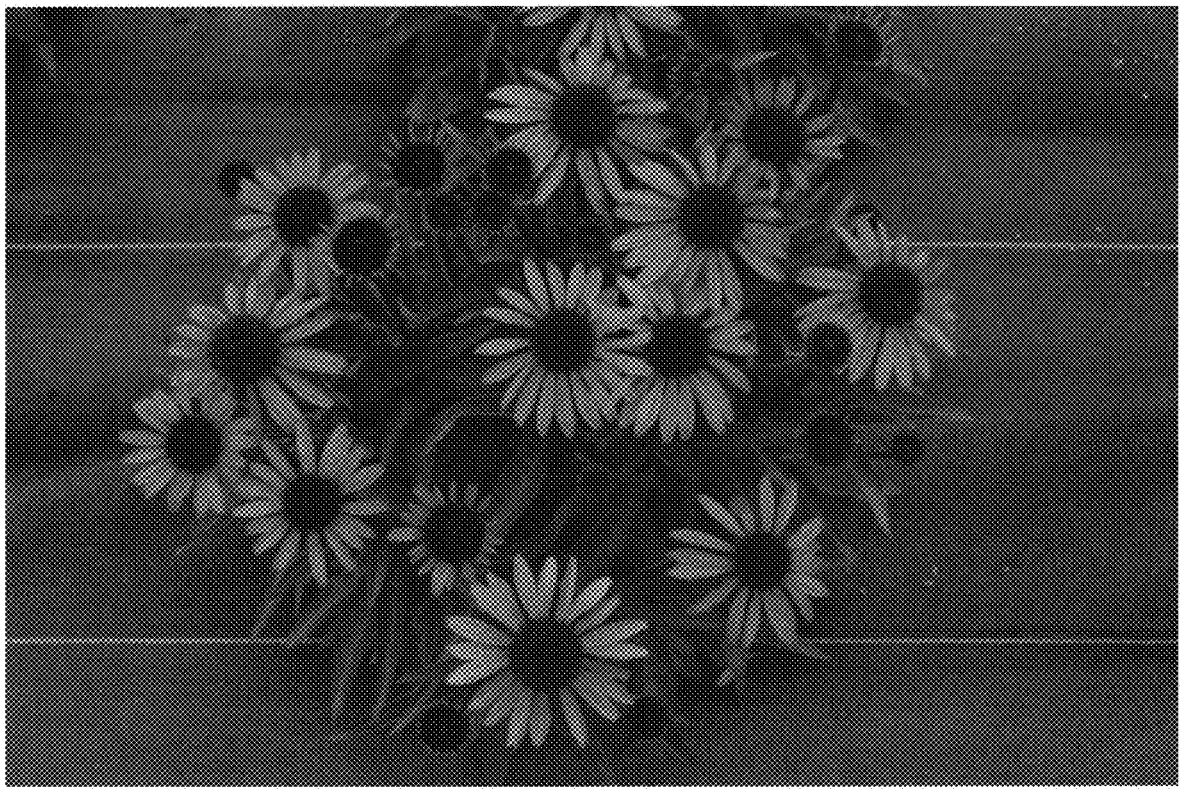
FIG. 2 shows a view from the top of a nine-month-old *Echinacea* 'TNECHDSW' growing in the trial field in full sun in late July in Canby, Oreg.

The following is a detailed description of the new *Echinacea* cultivar based on observations of 9-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The Royal Horticultural Society Colour Chart, $5^{th}$ edition, 2007.

Plant:

*Type.*—Herbaceous perennial.
*Hardiness.*—USDA Zones 4 to 9.

*Size.*—Grows to 31 cm wide and 37 cm tall to top of inflorescences.

*Form.*—Basal clump, with 7 to 12 stems from the base.

*Vigor.*—Excellent.

*Roots.*—Fibrous, with many downward growing and few laterals, ivory to cream in color, Yellow White 158D, roots develop easily from cuttings from the crown.

Leaf (basal):

*Type.*—Simple.

*Shape.*—Lanceolate.

*Arrangement.*—Rosette.

*Blade size.*—Grows to 16 cm long and 5 cm wide.

*Margins.*—Entire.

*Apex.*—Acuminate.

*Base.*—Attenuate.

*Surface texture.*—Strigose on both sides.

*Venation.*—Pinnate, Yellow Green 145D on both sides.

*Color.*—Topside Green N137B, bottom side closest to Yellow Green N137B.

*Petiole description.*—Clasping, grows to 13 cm long and 4 mm wide, scabrous, narrow leafy edges, topside Yellow Green 147B with Red Purple 59B at base, bottom side closest to Yellow Green 147C tinted Red Purple 59B at base.

Leaf (stem):

*Type.*—Simple.

*Shape.*—Lanceolate.

*Arrangement.*—Alternate.

*Blade size.*—Grows to 13 cm long and 3.5 cm wide.

*Margins.*—Mostly entire.

*Apex.*—Acuminate.

*Base.*—Attenuate.

*Surface texture.*—Strigose on both sides.

*Venation.*—Pinnate, Yellow Green 145C on both sides.

*Color.*—Topside Green N137A, bottom side closest to Yellow Green 147A.

*Petiole description.*—Clasping, grows to 4 cm long and 3.5 mm wide, scabrous, narrow leafy edges, topside Yellow Green 147B, bottom side Yellow Green 147C.

Inflorescence:

*Type.*—Composite on terminal stalked heads.

*Flowering stem.*—Grows to 28 cm tall from the base of the plant to the terminal inflorescence; unbranched to branched, with 1 to 9 inflorescences per stem; diameter growing to 9 mm wide near the inflorescence; strigose; Yellow Green 147B in shade, tinted N77A in sun.

*Size.*—Grows to 9 cm wide and 5 cm deep as disc enlarges.

*Form.*—Ray florets held horizontally, reflexing somewhat in very old flowers, mature disc is conic.

*Immature inflorescence* (*bud*).—3 cm wide and 3 cm deep, ray florets held upright at a 70 degrees angle from vertical and rolled up so only the back color shows, Greyed Purple 189A except tip Greyed Yellow 160B, disc color Greyed Orange 165A except the center where Yellow Green 146B.

*Ray florets.*—Without pistil or stamen, about 18 in number, grow to 45 mm long and 15 mm wide, oblanceolate with the tip two-to-three-toothed (each acute), entire margins, base attenuate, glabrous on both sides; fully open florets topside Red-Purple, between 72C and 72D, bottom side Greyed Purple 186C; florets fade gradually from tip down to topside Greyed Purple 186D.

*Disc.*—Flat becoming conic, becoming 40 mm deep and 40 mm wide with maturity, Greyed Purple 187A in background with bracts Orange 26A with tips Greyed Purple 187A.

*Disc florets.*—About 232 in number, each with 1 pistil and 4 stamen, grow to 9 mm long and 2 mm wide, each with one persistent, very stiff linear bract (12 mm long with the top 1 mm Greyed Purple 187A to 2 mm Orange 28C to 1 mm Greyed Purple 187A to Yellow Green 147A blending to White NN155A on bottom); corolla 5 mm long and 2 mm wide, tubular, 5 lobed, glabrous and glossy, Yellow Green 152B at the base blending to Greyed Purple 187A on lobes; pistil 11 mm long, style 6 mm long White NN155A, 2-branched stigma spreading 3 mm wide, Greyed Purple 187A; stamen 4 mm long, filaments 2 mm long and White NN155B, anthers 2.5 mm long and Yellow Green 152B, pollen Yellow 17C.

*Involucral bracts.*—In 4 to 5 leafy series, area grows to 35 mm wide and 15 mm deep, lobes lanceolate in shape, reflexed, grow to 13 mm long and 4 mm wide, Green 137B, margins strigose, tip acute, strigose on both sides.

*Receptacle.*—Grows to 13 mm wide and 19 mm deep, White NN155B.

*Bloom period.*—June through October in Canby, Oreg.

*Fragrance.*—Slight.

*Lastingness.*—Each inflorescence lasts about two weeks in Canby, Oreg.

Seeds: 3 mm long and 2.5 mm wide, oval, Brown 200C.

*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *